United States Patent [19]

Levesque et al.

[11] Patent Number: 4,870,016

[45] Date of Patent: Sep. 26, 1989

[54] PROCESS OF CHEMICAL MODFICATION OF PROTIDES AND THE PRODUCTS THUS MODIFIED

[76] Inventors: Guy Levesque, 19 rue de l'Unité Epron, F-14610 Thaon; Jerome Souppe, 3 rue de Batsalle, F. 64000 Pau; Jean L. Séris, Lot. Parenche-Chemin Vignats, F64110 Jurancon; Valerie Bellenger, 39 rue de la Tigaciere, F. 14000 Caen, all of France

[21] Appl. No.: 213,093

[22] Filed: Jun. 29, 1988

[30] Foreign Application Priority Data

Jun. 30, 1987 [FR]  France ................................. 87 09198
May 25, 1988 [FR]  France ................................. 88 06914

[51] Int. Cl.$^4$ .......................... C12N 9/00; C12N 9/50
[52] U.S. Cl. ..................................... 435/183; 435/219

[58] Field of Search ................................. 435/183, 219

[56] References Cited

U.S. PATENT DOCUMENTS 4,609,625  9/1986  Keyes ................................. 435/183

*Primary Examiner*—Peter D. Rosenberg
*Attorney, Agent, or Firm*—Ostrolenk, Faber, Gerb & Soffen

[57] ABSTRACT

Process of modification of a protide by fixation of an organic group to its molecule, comprising reacting the protide with a dithioic acid, salt or ester, the acid residue of which comprises the organic group to be fixed, while the remainder of the molecule has a leaving group structure, such that the dithioic compound reacts with the —NH$_2$ or —NH— of the protide molecule.

21 Claims, No Drawings

PROCESS OF CHEMICAL MODIFICATION OF PROTIDES AND THE PRODUCTS THUS MODIFIED

The present invention relates to a new process for the chemical modification of protides. It comprises a reaction allowing the fixation to the protide molecule of one or more organic groups, capable of changing the physico-chemical properties of the protide. The invention envisages particularly the modification of proteins and, in particular, those of enzymes. An important use of the invention lies in changing the solubility of peptides or proteins and especially in rendering enzymes soluble in organic solvents.

The invention also comprises protides carrying organic groups, modifying their physico-chemical properties. It envisages in particular enzymes rendered soluble in organic solvents, by the fixation of such groups.

It is known to change to a greater or lesser extent the properties of a protein by the action of a chemical reactant. In the case of enzymes, this generally has the purpose of modifying their physical properties, such as solubility, mobility, that is to say the molecular weight, stability etc. Attempts have also been made by this means to render possible the use of these remarkable catalysts under less drastic conditions than those which require the native enzyme, particularly pH, temperature, ionic force, resistance to inhibitors etc. Other objectives lie in modification of the catalytic properties themselves, namely enlargement of the range of substrates suitable for the given enzyme or, on the contrary, in orientation of the catalytic activity in the sense of a greater specificity; this can concern for example rendering a protease more specific to a certain peptide bond if it hydrolyses in the native state too large a spectrum of peptides or the use of enzymes in a nonaqueous medium or at a lower concentration in water which is capable of reversing the direction of reactions in which water participates.

Most of the known processes of chemical modification of proteins consist in using specific compounds, capable of reacting with the functional groups carried by the residues of natural amino acids of the peptide chain or by the glucidic or nucleic part of glycoproteins or nucleoproteins. Thus use is frequently made of the nucleophilic power of the ε—NH₂ group of lysine residues on activated electrophilic reactants. The reactants most often utilised in the prior art are acid anhydrides and trinitrobenzenesulphonic acid. Enzymes modified by these known processes generally have a substantially reduced activity. The choice of reactants is very restricted because many reactants eventually alter the activity of the enzyme too much or even require operative conditions incompatible with conservation of the catalytic activity or react with other amino acids essential for maintenance of the active structure of the enzyme.

In view of the interest in the appropriate modification of protides, in particular of enzymes, the need for adequate reactants continues to arise.

The present invention provides a substantial advance in this field; it relates to a class of compounds which have the property of reacting easily with the amino residues of protides to fix on them any desired organic group, while not reducing or only relatively slightly affecting the catalytic activity, when the protide is an enzyme, and rendering it soluble in an organic solvent.

The process of the invention is characterised in that the given protide is reacted with a dithioic acid, salt or ester, the acid residue of which comprises the organic group which is to be fixed to the protide, while the remainder of the molecule has a leaving group structure.

The dithioic ester, acid or salt employed can be represented by the formula

where R designates the organic group to be fixed, through the intermediary of C=S to the protide, while X is H or a cation or a group selected in such a manner that X-S is a good leaving group.

By designating with E the molecule of the protide, the reaction according to the invention can be written as follows:

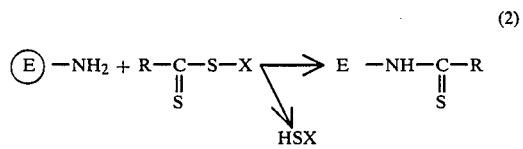

Thus, HSX being eliminated, the protide molecule is modified by fixation of one or more of the groups

This modifier group is naturally chosen according to the new properties which it is desired to impart to the protide, for example solubility in hydrocarbons, reactivity with bases, resistance to heat, etc. It can thus concern an R which is an aliphatic or aryl hydrocarbon radical, and thus hydrophobic, in particular $C_1$ to $C_{20}$ alkyl or $C_2$ to $C_{20}$ alkenyl, phenyl, phenylenyl, naphthyl or naphthylenyl or a corresponding alkylaryl or arylalkyl. R can also be a polar hydrophilic negative, positive or neutral organic group; thus for example it can comprise a carboxyl, hydroxyl, halogen, sulphinyl, sulphonyl, phosphoryl, phosphonyl, sulphydryl, amide, ammonium, phosphonium or other group.

In a particular embodiment, R is a polymer or oligomer chain, for example of polyethylene, polypropylene, polyacrylic, polyethylene glycol or similar.

Otherwise, R can be constituted itself by a residue of a dithioester of the type

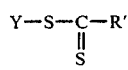

in which R' designates a divalent hydrocarbon group, particularly alkylene, cycloalkylene, arylene or alkylarylene, the first preferably comprising 1 to 20 carbon atoms and the others 6 to 16. Y is a group of the same type as X but not necessarily identical therewith. In this variant, the reactant is a bis-dithioester:

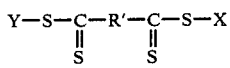 (3)

Use of a bis-dithioester allows formation of a modified special protide, carrying a polymer chain, in particular polyacrylic, polyvinylic alcohol, polyalkyleneglycol or other oligomer or polymer capable of being aminated at least at the end of the chain. By designating with Q-NH$_2$ such an aminated polymer, it can be combined with the bis-dithioester by a reaction

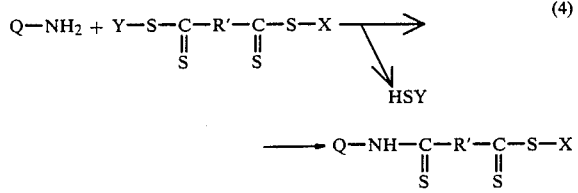 (4)

Thus, by reacting the compound of Q obtained in (4) with a protide

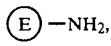, the reaction leads to:

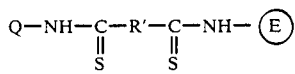 (5)

that is a bis-thioamide both of the polymer Q and the protide E.

By way of non-limitative illustration, there are given below the formulae of several of these dithioesters and bis-dithioesters utilisable in carrying out the present invention.

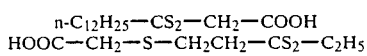

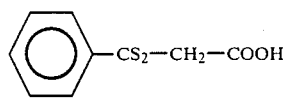

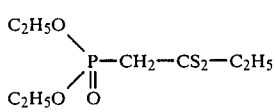

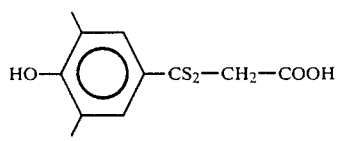

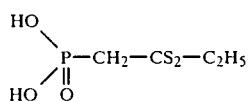

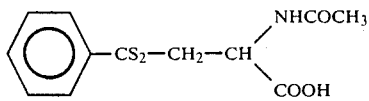

-continued

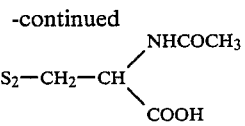

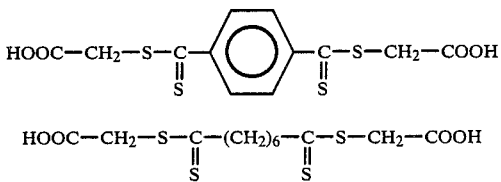

Depending upon the nature of the protide to be treated and that of a dithioester employed, the process according to the invention is carried out in aqueous, organic or hydro-organic solution, generally at a temperature in the range from 0° to 70° C. In the case of enzymes, the preferred temperatures range from 10° to 50° C. and in particular from 20° to 45° C.

The proportions of the reactants are calculated starting from the number of —NH— or —NH$_2$ groups of the protide which are to be combined with the dithioester. It is good practice in general to utilise an excess of the dithioester functions per free —NH— or —NH$_2$ group on the protide to which the modifier group is to be fixed. The reaction medium can if required be heterogeneous, comprising for example a dispersion of the protide in an organic solution of the dithioester; this in particular is the case where the reaction according to the invention solubilises the protide in the organic solvent of the dithioester; thus the protide, having undergone the reaction, passes into solution in this solvent.

In a variant, X and/or Y, the same or different, are constituted by a hydrocarbon part (—CH$_2$)$_n$, where n is 1 to 6, carrying a halogen, carboxyl, sulphinic, sulphonic, phosphorous, phosphonous, phosphoric, phosphonic, active H, SH, amide or hydroxy function.

A protide according to the invention, in particular a protease or peroxidase, soluble in benzene, toluene, ether, ethanol, chloroform and/or dimethylsulphoxide, comprises several lysine groups which carry, through the intermediary of a

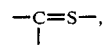, an R group constituted by a C$_1$ to C$_{20}$ aliphatic radical, a C$_6$ to C$_{16}$ aryl radical or a polymer chain, in particular polyethylene glycol.

When X in the formula (1) is a hydrogen atom, that is the dithioic compound is a dithioacid R-CSSH, R can be one of the radicals defined above. It is particularly convenient in carrying out the invention if the acids R-CSSH and their amine or quaternary ammonium salts have a R group which is a C$_4$ to C$_{18}$ alkyl, for example n-C$_4$H$_9$ or n-C$_{11}$H$_{23}$-, a phenyl or tolyl —C$_6$H$_5$, CH$_3$—C$_6$H$_4$ etc.

The dithioic acid salts suitable for the invention have a cation derived from a weak base. The weak base, the dithioacid salt R-CSS-X of which is utilisable according to the invention, can be such as ammonia, hydrazine, hydroxylamine, piperidine, primary, secondary or tertiary amine, di- or tri-amine, pyridine, tetra-alkyl ammonium, di- or tri-alkyl respectively di- or mono aryl ammonium or hydroxide of Zn, Al, Mn, Pb, etc. and, in a general manner, any base having an ionic dissociation constant in water at ordinary temperature which is preferably of the order of $10^{-10}$ to $10^{-3}$ and especially from $10^{-6}$ to $10^{-4}$. Thus use can be made by way of non-limitative examples of salts in which X is the cation of ammonium, tetra methyl-ammonium, phenyl-triethyl ammonium, trimethylhexadecyl ammonium, monoethanolamine, di-ethanol amine, dipropylamine, di-isopropylamine, piperazine, tri-isobutyl amine, triethylamine, benzylamine, phenylethyl amines, etc.

Grafting according to the invention is effected by contacting the selected protide with the dithioic compound in a buffer solution of appropriate pH. It is useful to employ a large excess of this compound with respect to the protide, preferably from 10 to 100 equivalents of R-C-S-S-X per $NH_2$ group available in the protide. This excess is eliminated from the final solution, notably by dialysis. It is suitable to prolong this contact for several hours, most often and depending on the temperature and the nature of the reactants present, for 1 to 20 hours, while this indication is in no way limitative. It will be understood that regard must be had to the stability of the protide under the operative conditions, so that reaction is not prolonged beyond the stability of the product.

In a general manner, the process of the invention can be carried out in media of pH 3 to 11.5 and particularly from 4 to 9. However there are certain preferred regions depending on the nature of the protide treated and that of the dithioic compound used. Thus is it recommendable to operate with a pH not exceeding 7, when working with protides which do not easily tolerate a basic medium. On the other hand, good results are obtained with dithioic compounds R-CSSX constituted by a dithioester, when the pH is from 7 to 11.5 nd particularly pH 8 to 11. In contrast, when X is H or a weak base cation, the preferred pH values range from 3 to 7 or better still from 3.5 to 6.5 with in general an optimum of 4 to 6.

The examples which follow indicate without limitation details of the carrying out of the invention.

EXAMPLE 1

The operations described here serve to show (I) that it is possible to prepare one dithioester from another, by simply changing the nucleofuge, and (II) consequently how the —$NH_2$ of an amino acid reacts with a dithioester.

I. Preparation of S-dithiobenzoyl N-acetyl cysteine (DTAC)

2 ml of an M aqueous solution of NaOH is added to 1.632 g of N-acetyl cysteine and 2.123 g of thiobenzoylmercaptoacetic acid (or carboxymethyl dithiobenzoate) dissolved in 50 ml of ethanol. The mixture is agitated at 20° C. for 2 hours and then concentrated by evaporation of the ethanol and acidified with 6N HCl.

By chromatography on silica with a hexane/chloroform mixture as eluant, 2.45 g of S-thiobenzoyl-N-acetyl-cysteine is isolated, which represents a yield of 86.5% with respect to the initial acetyl cysteine, by the reaction:

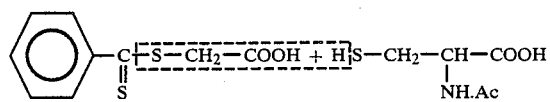

Thiobenzoyl mercaptoacetic acid      Acetyl-cysteine

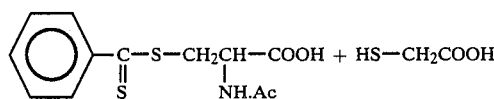

S—dithiobenzoyl-N—acetyl-cysteine (DTAC)      Mercapto-acetic acid

II. Preparation of N-thiobenzoyl-lysine starting with dithioobenzoyl-acetyl-cysteine (DTAC)

0.425 g or 1.5 mmole of DTAC prepared according to I and 0.220 g of lysine, also 1.5 mmole, are dissolved in 10 ml of 0.25 N aqueous NaOH solution. The solubilisation of the mixture is facilitated by the addition of a drop of ethanol. After 5 hours of reaction at ambient temperature, the medium is acidified and N-thiobenzoyl-lysine is liberated.

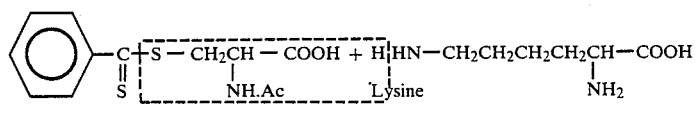

DTAC

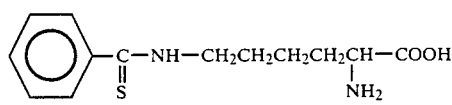

N—thiobenzoyl-lysine

EXAMPLE 2

Modification of horseradish peroxidase by means of tridecyl thiomercaptoacetic acid

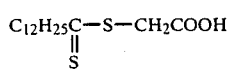

(i.e. carboxymethyl)

6 mg of commercial horseradish peroxidase (Sigma type II) or 0.15 μmole (after absorption of 402 nm with $\epsilon = 102$ mM$^{-1}$.cm$^{-1}$) and 1.6 mg of tridecyl thiomercaptoacetic acid or 5 μmoles (previously dissolved in 0.1 ml of ethanol) are dissolved in 3 ml of 0.1M phosphate buffer, pH=8.5. The mixture is agitated for 18 hours at ambient temperature. The solution is then dialysed for 18 hours at 4° C. against distilled water and then lyophilised. The enzyme obtained has been analysed. It has the following characteristics.

UV spectrum: appearance of a band at 277 nm due to the thioamide functions formed.

Number of lysines affected: the free lysines are measured by the classic TNBS method (trinitrobenzenesulphonic acid) and thus 3 to 4 lysines which have been affected were found.

Solubilities: whilst the native enzyme is not soluble in water, the new enzyme is soluble to more than 5 mg per ml in ethanol, chloroform, toluene, ether and water.

Specific activity: this is the activity measured on the oxidation of orthodianisidine with oxygenated water. A dimer is formed which absorbs at 444 nm (with $\epsilon = 30$ mM$^{-1}$.cm$^{-1}$). The specific activity obtained is 850 U per mg of protein or 97% of the specific activity of the native enzyme.

Activity in organic solvent: the horseradish peroxidase is known to catalyse the oxidation reaction of 9-methoxy-ellipticine:

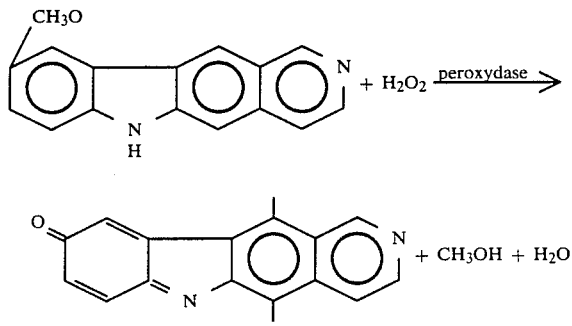

This reaction is of interest because 9-oxoellipticine is easily reduced to 9-hydroxyellipticine with ascorbic acid. The sole disadvantage resides in the poor solubility of 9-methoxyellipticine in water. The low substrate concentration which results for the enzyme limits the speed of the oxidation reaction.

Thus this reaction can be put into operation in ether with the peroxidase modified according to the invention. In a spectrophotometer vessel, 0.5 ml of 9-methoxyellipticine 1 mM in ether, 0.5 ml of modified peroxydase 1 mg per ml in ether, 10 to 50 µl of an aqueous solution of 200 mM oxygenated water were mixed together and completed with ether up to a final volume of 2 ml. Then at 20° C. absorbance occurs at 486 nm, the wavelength of absorption of the 9-oxoellipticine formed ($\epsilon = 9.2$ mM$^{-1}$.cm$^{-1}$). Several tests effected with different quantities of oxygenated water have shown that the oxidation kinetic is michaelien with:

| | |
|---|---|
| $K_m^{H2O2}$ = | 2 mM |
| $V_m$ = | 0.25 µmol/mn per mg of lyophilisate of modified peroxidase |

EXAMPLE 3

Fixation of thiobenzoic groups to papain rendering it soluble and active in dimethyl sulphoxide 0.32 g of commercial papain (Sigma Type IV) and 100 mg of thiobenzoyl-mercapto-acetic acid previously dissolved in 3 ml of ethanol are dissolved in 40 ml of 0.1M phosphate buffer, pH=8.5. The mixture is left for 2 hours at 40° C. and then dialysed for 16 hours at 4° C. against water and then lyophilised. 0.26 g or 81% of the chemical yield is recovered. The enzyme obtained has the following characteristics.

UV spectrum: displacement of the absorption band from 278 nm to 280 nm.

Number of lysines affected: 2 out of the 10 contained in papain.

Solubility: soluble in benzene, DMSO and water at a rate of 10 mg per ml while the native enzyme is not soluble in benzene, only in water and in DMSO.

Amidase activity: under hydrolysis at pH=7.5 and at 50° C. in a tris buffer and in the presence of cysteine and EDTA, N-benzoyl-D,L-arginine-paranitroanilide (BAPA) liberates para-nitroaniline absorbing at 410 nm (with $\epsilon = 8.8$ mM$^{-1}$.cm$^{-1}$). Whilst the native enzyme has an activity of 28 mU per mg of lyophilisate, the modified enzyme has 11 mU per mg of lyophilisate or 32% of the initial activity; despite this the modified enzyme is very interesting because it has an activity in an organic solvent; it can thus be utilised in DMSO in the absence of water for peptide synthesis. DMSO is particularly suitable to solubilise numerous peptides, but the native enzyme has no activity in this solvent; in contrast, the modified enzyme has an activity of 1.2 mU per mg of lyophilisate.

EXAMPLE 4

Modification of papain by the fixation of ethyl thiopropionate groups on its molecule The dithioester ethyl carboxymethyl 3-sulphide dithiopropionate

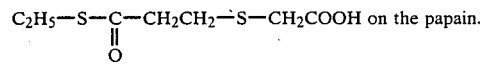

is reacted with papain in aqueous medium. For this, 36 mg of commercial papain (Sigma Type IV) is mixed with 23 mg of the dithioester previously dissolved in 0.1 ml of ethanol, in 4.5 ml of 0.1 phosphate buffer, pH=8.5. The mixture is taken to 40° C. for 2 hours, then dialysed for 16 hours at 4° C. against an 0.1M phosphate buffer, pH=7.2. The protein solution obtained is analysed and the following is found:

UV spectrum: maximum absorption displacement from 278 nm to 270 nm.

Number of lysines affected: 4.5 out of 10.

Enzymatic activity in water, loss of 50%.

The sites in the modified molecule can be represented, according to formula (II), by:

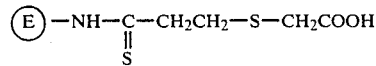

This example shows that a —$^+$NH$_3$ group can be replaced by a —COO$^-$ group, which allows the isoelectric point and the optimum pH range of the modified enzyme to be changed.

EXAMPLE 5

Fixation of a polyethylene glycol bis-dithioester (PEG-dithioester) on horseradish peroxidase A functionalised polymer is prepared in the following manner. 0.25 g of bis-amino commercial PEG 20000 (Sigma) corresponding to 25 µmoles of free NH$_2$ functions, is dissolved in 10 ml of distilled water; 0.4 ml of triethylamine and 44 mg of carboxymethyl tetrathiooctanedioate

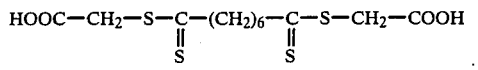

previously dissolved in 0.1 ml of ethanol are added; this represents 250 μmoles of the dithioester function. The pH is fixed at 10.8. The mixture is allowed to agitate for 48 hours at ambient temperature. The solution is then dialysed for 16 hours at ambient temperature against distilled water. 13 ml of a solution at pH=6.6 is recovered, which is analysed.

The UV spectrum allows the grafted dithioester functions to be measured at 3.08 nm (with $\epsilon=12.2$ nM$^{-1}$.cm$^{-1}$), and the thioamide functions formed at 263 nM ($\epsilon=12.8$ mM$^{-1}$.cm$^{-1}$). Having worked with an excess of the dithioester functions, it is clear that there are then no free —NH$_2$ functions. There is thus a product of the formula:

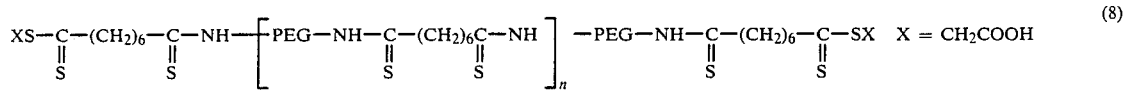

The ratio of the thioamide (1.31 mM) and dithioester (0.18 mM) function concentrations allows the degree of polymerisation n to be calculated; this ratio is $$r = \frac{2n+2}{2} = n+1$$

Experimentally the following has been obtained:

$$r = \frac{1.31}{0.18} = 7.3 \text{ or } n = 6.3$$

6 mg of commercial horseradish peroxidase (Sigma Type II) is dissolved in the solution previously prepared (0.15 μmole of peroxidase and 2.3 μmole of dithioester) and the pH is taken to 8.5 by dissolution of Na$_2$HPO$_4$ in the mixture. It is allowed to agitate for 18 ours at ambient temperature and then the solution is dialysed and finally lyophilised. The enzyme obtained has the following characteristics.

UV spectrum: appearance of a band at 287 nm due to the thioamide functions.

Number of lysines affected: 2.

Solubility: the enzyme is soluble to more than 5 mg per ml in the solvents acetone, chloroform, dioxane, toluene, dimethylformamide and water.

Specific activity; 780 U per mg of proteins or 89% of the specific activity of the native enzyme.

Activity in chloroform: for the oxidation of 97-methoxyellipticine, the activity is satisfactory. In a spectrophotometry vessel, 0.5 ml of 9-methoxyellipticine 1 mM in chloroform, 0.3 ml of peroxidase modified with 1 mg per ml in chloroform, 10 to 40 μl of oxygenated water at 200 mM (in aqueous solution) were mixed together and the volume was taken to 1.5 ml with chloroform. For different quantities of oxygenated water, a michaelian kinetic was observed with:

| | |
|---|---|
| $K_m^{H2O2}$: | 6.25 mM |
| $V_m$: | 83 nmoles/minute per mg of lyophilisate of modified peroxidase |

EXAMPLE 6

Modification of papain with the aid of a polyethylene glycol bis-dithioester

The functionalised polymer was prepared as in Example 5 but under conditions of greater dilution. The same quantities of the product were used in 100 ml of distilled water in place of 10 ml as in Example 5. A lighter polymer was obtained and UV measurement indicated n=O. Thus the following was obtained:

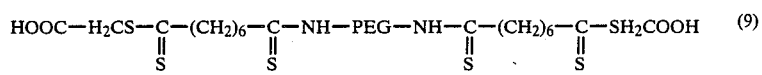

1.9 gm of commercial papain (Sigma Type IV) and 89 mg of Na$_2$HPO$_4$ are dissolved in 23 ml of the functionalised polymer solution indicated above. The volume is taken to 50 ml with distilled water. The pH obtained is 8.5. The solution is taken to 40° C. for 2 hours and then dialysed for 16 hours at 4° C. against distilled water. The dialysed solution has a pH=6.6 and a volume of 58 ml. After lyophilisation, 45 mg was recovered, i.e. a chemical yield of 76%. Analysis of the enzyme thus modified gives the following results.

UV spectrum: the band at 278 nm is displaced to 269 nm with a peak at 308 nm showing that all the dithioester functions have not reacted.

Number of lysines affected: 5 lysines out of 10.

Solubility: the enzyme is soluble to 10 mg per ml in chloroform, DMSO and water.

Amidase activity: 1.5 mU per mg of lyophilisate or a yield in activity:

$$\frac{45 \times 1.5}{1.9 \times 28} = 125\%$$

Activity in DMSO by the same tests as in Example 3: 3.0 mU per mg of lyophilisate. In chloroform, the substrate solution is prepared in a mixture of 80% of chloroform with 20% of DMSO to solubilise the ingredients necessary for the test. An activity of 4.2 mU per mg of lyophilisate was found. In contrast, the native enzyme put into suspension (because it is insoluble in chloroform) in an identical test shows no activity.

The two examples 5 and 6 show that modification with PEG-dithioesters allows good activities to be obtained in chloroform, which is a substantial technical advance.

EXAMPLE 7

Modification of a hemoprotein with dithiopentanoic acid

The treated protein is horseradish peroxidase having an isoelectric point of 7.2.

25 mg of horseradish peroxidase (Sigma Type II) and 2 mg of pure $CH_3(CH_2)_3CSSH$ dithioacid are dissolved in 5 ml of 0.2M phosphate buffer, pH 6.0, which corresponds to concentrations of 0.05 mM of enzyme per 3 mM of dithio-acid.

The mixture was left to agitate for 16 hours at ambient temperature. The solution was then dialysed for 16 hours against a 5 mM citrate buffer at pH 6.5.

The dialysate was then recovered and analysed:

The overall chemical yield is calculated by comparison with the number of moles of hemoprotein (determined by absorption at 402 nm where $\epsilon = 102$ $mM^{-1} = .cm^{-1}$) utilised initially with those of the moles recovered after modification. The yield is 100%. As regards activity, this was determined for each peroxidase solution with respect to the activity of the solution (in U per ml) with the concentration in hemoprotein (in nmole per ml) which leads to a specific activity in U per nmole of heme.

The enzymatic activity of the solution is measured at 30° C. in a plastic vessel filled with 0.1M of citrate buffer, pH 3.5, 20 µl of 0.2M oxygenated water, 20 µl of 13 mM orthodianisidine and 20 µl of the enzymatic solution previously diluted 20 times. The product of oxidation of the orthodianisidine is followed at 444 nm with $\epsilon = 30$ $mM^{-1}.cm^{-1}$. In the present example, a specific activity of 125 U/nmole of heme for the native enzyme is exceeded at 67 U/nmole of hame for the modified enzyme or 54% of the yield: since the chemical yield is 100%, the overall yield in activity is thus 54%. However the modifified enzyme has the advantage of presenting a ligninase activity of 1.4 U/µ mole of heme while the native enzyme has no activity.

The number of groups of lysine is determined by the TNBS method (trinitrobenzene-sulphonic acid): it is found that 3 lysines out of 6 have been modified with dithiopentanoic acid.

EXAMPLE 8

Modification of horseradish peroxidase with a salt of dithiobenzoic acid 2.6 mg of horseradish peroxidase (Sigma Type II) and 1.2 mg of tetramethylammonium dithiobenzoate

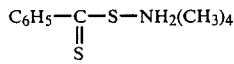

are dissolved in 100 ml of 0.1M citrate buffer at pH 5.0.

The initial concentrations thus are 0.26 µM of enzyme and 5.3 µM of dithioacid salt. After 2 hours of agitation at ambient temperature, the solution is dialysed for 16 hours, against a 5 mM citrate buffer at pH 6.0.

The analyses effected as in Example 1 give:
chemical yield 72%
overall yield in activity 110%
number of lysine groups grafted: 6.

It can be seen that the treatment according to the invention has increased the activity of the enzyme and that thiocarbonyls are fixed on all the lysine groups present.

EXAMPLE 9

Modification of the lignin peroxidase of Phanerochaete Chrysosporium with dithiopentanoic acid, $CH_3(CH_2)_3CSSH$ The protein utilised has an isoelectric point of 3.9.

To 80 ml of 0.2M phosphate buffer, pH 6.0, are added 20 ml of the crude preparation of lignin peroxidase obtained from a culture of Phanerochaete Chrysosporium (described in TIEN, M and KIRK, T K, 1984, Proc. Natl. Acad. Sci. US.81, 2280-2284) and 1.5 µl of the pure dithioacid. The concentrations in hemoprotein and dithioacid thus are 0.52 µM and 130 µM respectively.

The mixture is left under agitation for 7 hours at ordinary temperature and then dialysed for 40 hours against a bis-tris 1 mM buffer at pH 6.0.

The analyses are effected as in the foregoing Example 7 and 8:

chemical yield, determined by the absorbencies at 404 nm ($\epsilon = 102$ $mM^{-1}.cm^{-1}$), with modification, 73% with respect to the initial enzyme.

overall yield in activity: 65%; the activity can be determined at 30° C. in a plastic vessel containing 2 ml of 0.1M lactate buffer at pH 3.0, 0.1 ml of 10 mM oxygenated water, 0.1 ml of veratrilic alcohol and 0.1 ml of the enzymatic preparation, by the appearance of veratrilic aldehyde

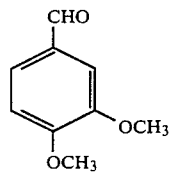

being followed at 310 nm requiring $\epsilon = 9.1$ $mM^{-1}.cm^{-1}$. The small reduction in the activity of the enzyme is compensated by the fact that the modified protein can by lyophilised, while the native enzyme loses all its activity on lyophilisation. The lyophilisate of the modified enzyme is soluble in chloroform and in DMSO.

EXAMPLE 10

Study of the effect of pH on modification of lignin peroxidase

Operation is with the same enzyme as in Example 9 and with the same dithiopentanoic acid.

20 ml of the crude preparation of lignin peroxidase and 2 µl of dithiopentanoic acid are added to 80 ml of 0.1M citrate-phosphate buffer at pH 3.0, 4.0, 5.0, 6.0 or 6.8. After 3½ hours of agitation at ambient temperature, the mixture is dialysed against 5 mM citrate phosphate buffer at pH 6.0 for 18 hours.

Results as a function of pH are given in the following table:

| pH | Chemical yield (%) | Overall yield in activity (%) |
| --- | --- | --- |
| 3.0 | 25 | 1 |
| 4.0 | 43 | 60 |
| 5.0 | 70 | 115 |
| 6.0 | 56 | 85 |
| 6.8 | 51 | 45 |
| 8.5 | 90 | 0 |

For all the tests, a total absence of free lysine groups is observed after modification with the dithioacid. It thus appears that pH 5.0 is optimal for this modification of lignin peroxidase. At this pH, the activity of the enzyme is augmented by the attachment of the $CH_3(CH_2)CS-$ groups. It is striking to see that if operation takes place at pH 8.5 as in Examples 2 to 4, the enzyme loses its activity with the dithiocompound employed here.

EXAMPLE 11

Modification of papain by dithiopentanoic acid Effect of pH

The isoelectric point of papain protease is 8.8. 36 mg of papain (Sigma Type IV) and 23 mg of the dithioacid are dissolved in 4.5 ml of 0.1M phosphate buffer, pH 6.0, 6.5 or 8.5. The mixture is heated to 40° C. for 2 hours and then dialysed at 4° C. for 16 hours against distilled water. The results as a function of pH are:

| pH  | Yield in activity (%) | Number of lysines affected |
|-----|-----------------------|----------------------------|
| 6.0 | 100                   | 6                          |
| 6.5 | 92                    | 3                          |
| 8.5 | 113                   | 0                          |

It appears clearly that the lower pH values favour the modification reaction. On the other hand, this example is important because papain is an enzyme of active cysteine. Since the activities are not in practice affected by modification of the dithioacid, it can be concluded that the cysteine at the active site of the protease is not attached by the dithioacid in the operative conditions, while the lysines are.

EXAMPLE 12

Modification of the lignin peroxidase of Phanerochaete Chrysosporium with a dithiobenzoic acid salt The protein is the same as in Example 9, of isoelectric point 3.9.

80 ml of 0.1M citrate buffer, pH 5.0, and 20 ml of the crude dialysed preparation of the lignin peroxidase are mixed together. Then 1.2 mg of tetramethyl-ammonium-dithiobenzoate is added. The initial concentrations in haemoprotein and the dithioacid salt thus are 0.46 $\mu M$ and 5.3 $\mu M$ respectively. After two hours of agitation at ambient temperature, the mixture is dialysed at 4° C. for 16 hours against a 5 mM citrate buffer at pH 6.0. The dialysate is analysed as described in Example 3, which gives:

chemical yield 100%.
overall yield in activity 86%
no free lysine after modification.

While the activity is somewhat lowered, the grafted enzyme has the advantage of being particularly stable; while the native enzyme loses 2 to 5% of its activity per month stored under the same conditions, the modified enzyme retains 100% of its activity after 2 months.

EXAMPLE 13

Comparative

Grafting of papain (isoelectric point 8.8) is effected as in Example 6, but at pH 6 in place of 8.5; it is then found that the dithioester employed is not fixed to the protein. By contrast, as seen in Example 11 above, the dithioic acid is fixed to all the lysine groups at pH 6.

We claim:

1. Process of modification of a protide by fixation of a organic group to its molecule, in which the protide is reacted with a dithioic acid, salt or ester, the acid residue of which comprises the organic group to be fixed, while the remainder of the molecule has a leaving group structure, such that the dithioic compound reacts with the $-NH_2$ or $-NH-$ of the protidic molecule.

2. Process according to claim 1, wherein the dithioic compound correspond to the formula

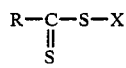

where R designates the organic group to be fixed through the intermediary of C=S to the protide, while X is a group eliminatable by the reaction of -S-X with an amine residue of the protide.

3. Process according to claim 2, wherein R is an aliphatic or aryl hydrocarbon radical.

4. Process according to claim 2, wherein R is a hydrophilic organic group.

5. Process according to claim 2, wherein R is a polymer or oligomer chain.

6. Process according to claim 2, wherein R is

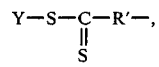

R' designating a divalent hydrocarbon group, while Y is a group eliminatable by the reaction of -S-Y with an amine residue of the protide.

7. Process according to claim 2, wherein X is $(-CH_2-)_n$, where n is 1 to 6, carrying a halogen, carboxyl, sulphinic, sulphonic, phosphorous, phosphonous, phosphoric, phosphonic, active H, SH, amide or hydroxy moiety.

8. Process according to claim 2, wherein X is a hydrogen atom or a cation of a weak base.

9. Process according to claim 1, wherein it is carried out in an aqueous, organic or hydro-organic solvent or in a heterogeneous medium between 0° and 70° C., the pH of the medium ranging from 3 to 11.5.

10. Process according to claim 9, wherein pH of the reaction medium is from 7.0 to 11.5 when the dithioic compound is a dithioester and from 3 to 7 when the compound is a dithioic acid or a salt of a weak base of such an acid.

11. A protide having at least one of the nitrogen atoms thereof carrying a group

where R is an organic radical.

12. Protide according to claim 11, comprising an enzyme which is soluble in organic solvents.

13. Protide according to claim 12, which s a protease or peroxidase soluble in at least one of benzene, toluene, ether, ethanol, chloroform and dimethyl sulphoxide, several lysine groups of which carry, through the intermediary of a

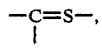

group R comprising a $C_1$ to $C_{20}$ aliphatic radical, a $C_6$ to $C_{16}$ aryl radical or a polymer chain.

14. Protide according to claim 12, comprising an enzyme, capable of catalysing an inverse reaction.

15. Protide according to claim 14, which is a hydrolase capable of catalysing the synthesis of esters, amides, thioamides and peptides.

16. Protide according to claim 13, where R is derived from polyethylene glycol.

17. Process according to claim 3, where R is a $C_1$ to $C_{20}$ alkyl, $C_2$ to $C_{20}$ alkenyl, phenyl, phenylenyl, naphthyl, naphthylenyl, alkylaryl or aryl-alkyl.

18. Process according to claim 4, where R comprises a carboxyl, hydroxyl, halogen, sulphinyl, sulphonyl, phosphoryl, phosphonyl, sulphydryl or amide moiety.

19. Process according to claim 5, where R comprises polyethylene, polypropylene, polyacrylic, polyethylene glycol or polyvinyl alcohol chain.

20. Process according to claim 6, where R' comprises a $C_1$ to $C_{20}$ alkylene or a $C_6$ to $C_{16}$ cycloalkylene, arylene or alkyl-arylene.

21. Process according to claim 9, where the temperature is from 20° to 45° C. and the pH is from 4 to 9.

* * * * *